United States Patent
Vertoprakhov et al.

(10) Patent No.: US 9,874,436 B2
(45) Date of Patent: Jan. 23, 2018

(54) HOLE INSPECTION METHOD AND APPARATUS

(75) Inventors: Victor Vertoprakhov, Singapore (SG); Tian Poh Yew, Singapore (SG)

(73) Assignee: VisionXtreme Pte Ltd., Singapore (SG)

( * ) Notice: Subject to any disclaimer, the term of this patent is extended or adjusted under 35 U.S.C. 154(b) by 696 days.

(21) Appl. No.: 13/003,247

(22) PCT Filed: Jul. 9, 2009

(86) PCT No.: PCT/SG2009/000246
§ 371 (c)(1),
(2), (4) Date: Feb. 10, 2011

(87) PCT Pub. No.: WO2010/005399
PCT Pub. Date: Jan. 14, 2010

(65) Prior Publication Data
US 2011/0128368 A1    Jun. 2, 2011

(30) Foreign Application Priority Data
Jul. 10, 2008  (SG) .............................. 200805209-4

(51) Int. Cl.
*H04N 7/18*     (2006.01)
*G01B 11/22*    (2006.01)
(Continued)

(52) U.S. Cl.
CPC .......... *G01B 11/22* (2013.01); *G01B 11/2425* (2013.01); *G01N 21/954* (2013.01)

(58) Field of Classification Search
CPC ... G01B 11/22; G01B 11/2425; G01N 21/954
(Continued)

(56) References Cited

U.S. PATENT DOCUMENTS 4,914,289 A * 4/1990 Nguyen ............. G01N 21/8806
                                                   250/223 B
5,408,538 A * 4/1995 Kitakado ............. G01N 21/956
                                                   348/126
(Continued)

FOREIGN PATENT DOCUMENTS

JP    61270600 A  * 11/1986
JP    08178858 A  *  7/1996
(Continued)

OTHER PUBLICATIONS

Patent Cooperation Treaty, "PCT International Search Report and Written Opinion of the International Search Authority" for International Application No. PCT/SG2009/000246, International Filing Date Jul. 9, 2009 (dated Feb. 19, 2010).

(Continued)

*Primary Examiner* — Jay Patel
*Assistant Examiner* — Joseph Suh
(74) *Attorney, Agent, or Firm* — Leif R. Sloan; Sonya C. Harris (57) ABSTRACT

An inspection apparatus initially involves an illuminator for directing an illuminating light beam towards a hole having two extremities and an internal surface extending between the two extremities. The inspection apparatus also involves a lens assembly for imaging the internal surface of the hole into the flat image. The lens assembly has a cylindrical field of view as well as a cylindrical depth of view. The cylindrical depth of field extends at least between the two extremities of the hole. The inspection apparatus further involves an image capturing device for capturing the flat image, and an image processing unit for performing inspection of the flat image to thereby inspect the internal surface of the hole. More specifically, the internal surface of the hole (Continued)

between the two extremities thereof is substantially in-focus along the flat image.

23 Claims, 7 Drawing Sheets

(51) Int. Cl.
 *G01B 11/24* (2006.01)
 *G01N 21/954* (2006.01)
(58) Field of Classification Search
 USPC .......................... 348/128, 86, 147; 382/149
 See application file for complete search history.

(56) References Cited

U.S. PATENT DOCUMENTS

| | | | | |
|---|---|---|---|---|
| 5,812,693 | A * | 9/1998 | Burt ..................... | H05K 13/08 348/129 |
| 5,905,595 | A * | 5/1999 | Minami ............... | G01N 21/8806 356/241.1 |
| 6,324,298 | B1 * | 11/2001 | O'Dell ................ | G01N 21/9501 257/E21.53 |
| 8,014,586 | B2 * | 9/2011 | Sones .................. | G01N 21/909 348/125 |
| 8,395,661 | B1 * | 3/2013 | Olsson ................ | G02B 23/2484 348/207.99 |
| 2005/0105774 | A1 * | 5/2005 | Kreuter ................... | G06K 1/02 382/112 |
| 2006/0209299 | A1 * | 9/2006 | Vertoprakhov .... | G01N 21/8806 356/237.5 |
| 2006/0232769 | A1 * | 10/2006 | Sugihara .......... | G01N 21/95692 356/237.2 |
| 2006/0243708 | A1 * | 11/2006 | Ikenoue ............... | B23K 26/032 219/121.62 |
| 2007/0002315 | A1 * | 1/2007 | Ban ....................... | G01N 21/954 356/237.1 |
| 2008/0094617 | A1 * | 4/2008 | Diehr .................... | G01N 21/90 356/240.1 |
| 2008/0186384 | A1 * | 8/2008 | Ishii .......................... | G06T 7/80 348/187 |
| 2008/0285055 | A1 * | 11/2008 | Niini .................... | G01B 11/105 356/602 |
| 2011/0128368 | A1 * | 6/2011 | Vertoprakhov ........ | G01B 11/22 348/86 |

FOREIGN PATENT DOCUMENTS

| | | | |
|---|---|---|---|
| JP | 2001-56299 | A | 2/2001 |
| JP | 2002-277402 | A | 9/2002 |
| JP | 2002277402 | A * | 9/2002 |
| JP | 2005-181144 | A | 7/2005 |

OTHER PUBLICATIONS

Patent Cooperation Treaty, "Notification Concerning Availability of the Publication of the International Application" for International Application No. PCT/SG2009/000246, International Filing Date Jul. 9, 2009 (dated Jan. 14, 2010).

Patent Cooperation Treaty, International Publication No. 2010/005399 A3, International Publication dated Jan. 14, 2010 for a Hole Inspection Method and Apparatus.

* cited by examiner

HOLE INSPECTION METHOD AND APPARATUS

FIELD OF INVENTION

The present invention generally relates to apparatuses and methods for inspection of an object. In particular, the invention relates to an apparatus and a method for inspecting internal surfaces of a hole in an object.

BACKGROUND

Many manufacturers routinely perform inspection on their manufactured products. This is typical of quality control measures where products that are defective are identified so as to control the quality of the manufactured products.

Many manufactured products require inspection on the products' interior surfaces, such as nut holes. Conventional methods of performing a hole inspection typically involve the use of a camera for capturing an internal surface of the hole. The camera and the manufactured product are usually rotated with respect to each other in order to obtain a complete all round view of the internal surface.

In many cases, the camera and the manufactured product are rotated by three hundred and sixty degrees relative to each other. The camera subsequently captures the complete all round view of the internal surface as the camera or product completes the rotation. The captured image of the interior of the manufactured product is then used to identify potential defects on the interior of the product.

However, the conventional methods of performing hole inspection are undesirably time consuming due to the time required for rotating the camera with respect to the manufactured product.

Additionally, the conventional methods of performing hole inspection are costly to implement because a rotating mechanism is required for rotating the manufactured product. The rotating mechanism also produces vibration that undesirably affects the quality of images obtained by the conventional methods.

Furthermore, conventional systems for performing hole inspection do not possess sufficient depth of focus. This results in defocusing of hole images captured by the conventional systems, and produces undesirable low quality images or unfocussed images. Unfocussed images are difficult to inspect as well as to extract crucial dimensional information because calibrating the unfocussed images results in poor pixel resolution characteristics.

Figure 6A:
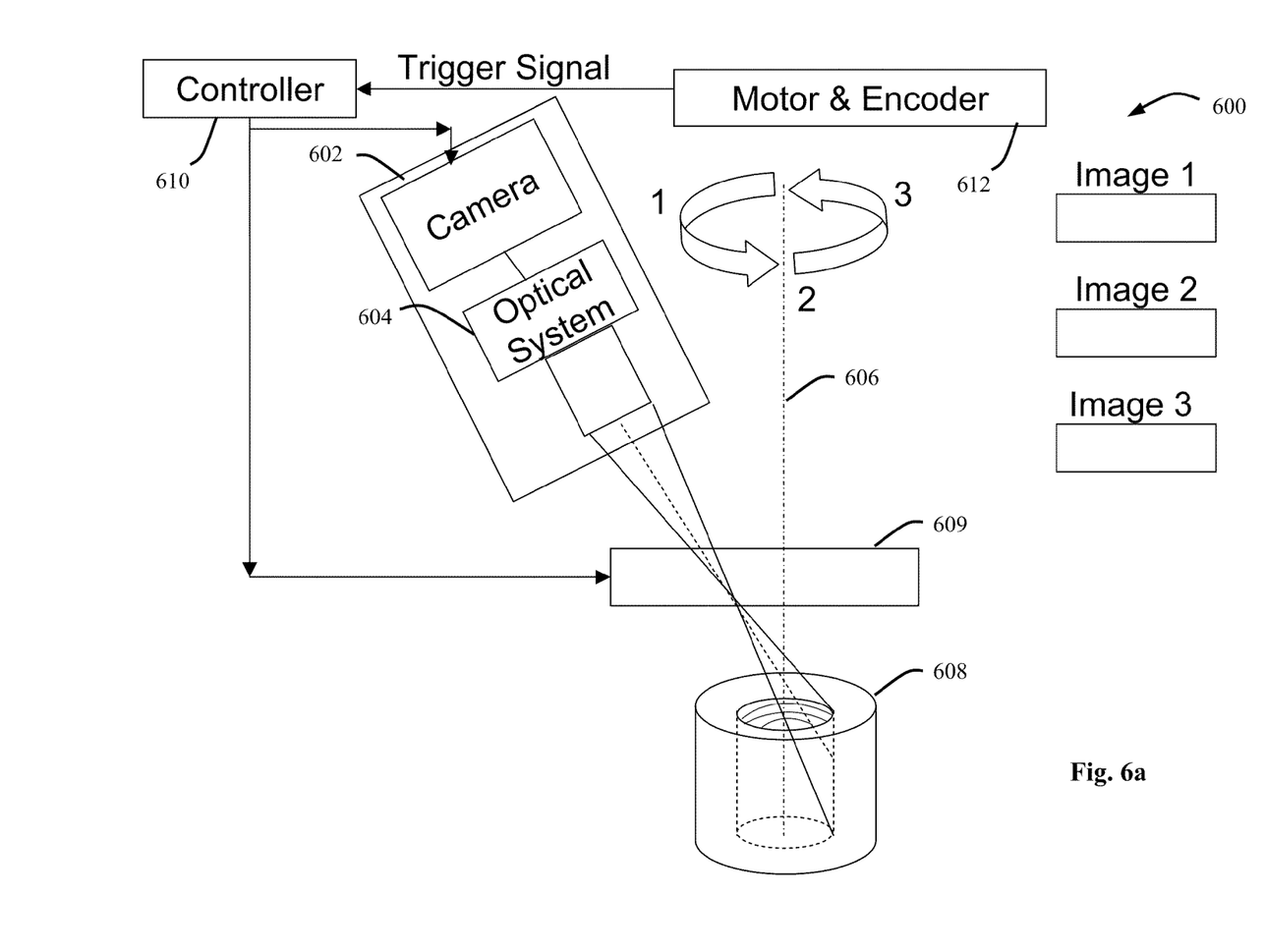
FIGS. 6a and 6b are schematic diagrams of prior art systems.
Figure 6B:
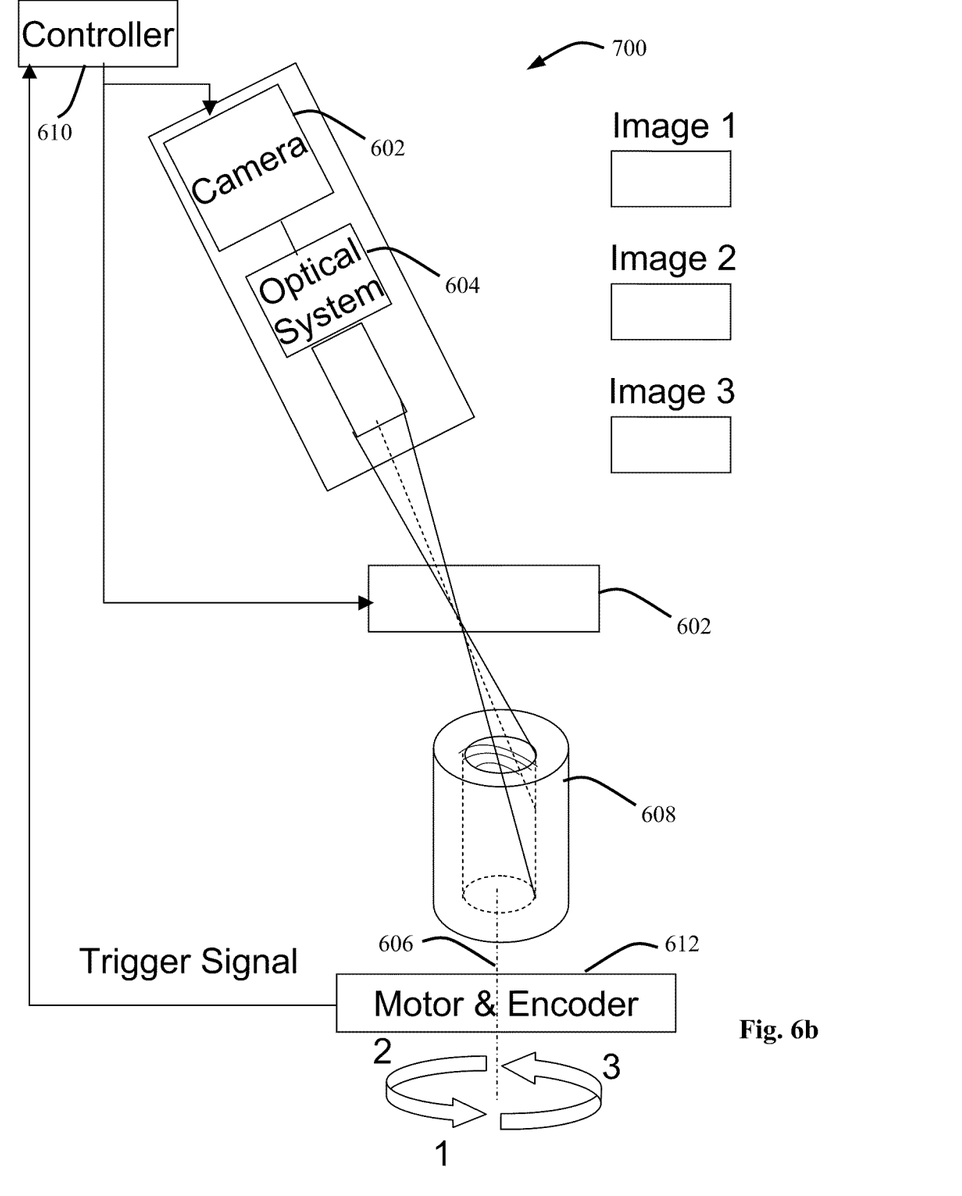

FIGS. 6a and 6b depicts prior art systems for hole inspection. With reference to FIG. 6a, an optical system 600 consisting of a camera 602 and an optical module 604 is mounted on a rotary mechanism (not shown) that rotates around a central axis 606. A rotary table (not shown) moves the optical module 604 to three different positions 1,2,3 where three images, namely image 1, image 2 and image 3 of an object 608 are captured. An illuminator 609 is used to illuminate the object 608. Depending on the purpose of the inspection or the object to be inspected, more of such positions can be setup to obtain more images. These images are subsequently inspected by a controller 610 that identifies defects in each of these images and determines if the object 608 is good or faulty by comparing inspected parameters with a golden template or through measurements of defects against limits set by end users.

FIG. 6b depicts another prior art system 700 wherein the object 608 is rotated instead of the optical module 604. This prior art system 700 is normally used for inspecting objects that have small to medium size and weight or in cases where the optical module cannot be rotated due to spatial or design limitations. In this prior art system, the object 608 is rotated while the optical module 604 captures images of the object 608 at several preset intervals to produce the same effect as the prior art system 600 of FIG. 6a.

In the foregoing prior art systems 600, 700, the time required to capture several images is not only undesirably long, the controller 610 is also required to process several images to produces images for inspection. Additionally the system cost of the foregoing prior art systems is undesirably high due to the need to use a motor and encoder module 612 to rotate the optical module 604 or the object 608. Information on the rotation of the optical module 604 or the object 608 is then fed back to the controller 610 for triggering the cameras 602 at appropriate trigger preset points.

There is therefore a need for inspecting internal surfaces of a hole in an object without requiring the object to be rotationally displaced and quickly arrive at a result by inspecting a single image of the entire internal surfaces of the hole.

SUMMARY

Embodiments of the invention disclosed herein involve inspecting internal surfaces of a hole in an object without requiring the object to be rotationally displaced.

Therefore, in accordance with a first embodiment of the invention, there is disclosed an inspection method. The inspection method comprises directing an illuminating light towards a hole having two extremities and an internal surface extending between the two extremities. The inspection method also comprises receiving light reflected and scattered from the internal surface through a lens assembly, the lens assembly having a depth of field extending at least between the two extremities of the hole. The inspection method further comprises capturing a flat image of the internal surface on an image plane, the internal surface being substantially in-focus along the flat image, and performing image processing and inspection of the flat image to thereby inspect the internal surface of the hole.

In accordance with a second embodiment of the invention, there is disclosed an inspection apparatus comprising an illuminator for directing an illuminating light towards a hole having two extremities and an internal surface extending between the two extremities. The inspection apparatus also comprises a lens assembly for receiving light beam reflected and scattered from the internal surface and for imaging the interior surface into a flat image, the lens assembly having a depth of field extending at least between the two extremities of the hole. The inspection apparatus further comprises an image capturing device for capturing the flat image of the internal surface on an image plane, the internal surface being substantially in-focus along the flat image, and a processor for performing image processing and inspection of the flat image to thereby inspect the internal surface of the hole.

BRIEF DESCRIPTION OF THE DRAWINGS

Embodiments of the invention are disclosed hereinafter with reference to the drawings, in which.

DETAILED DESCRIPTION

With reference to the drawings, embodiments of the invention relate to inspecting internal surfaces of a hole in an object without requiring the object to be rotationally displaced.

Conventional methods of performing inspection are undesirably time consuming due to the time required for rotating the object through three hundred and sixty degrees. Furthermore, conventional methods of performing inspection are also costly to implement because manipulation means is required for displacing the object and the inspection device relative to each other.

For purposes of brevity and clarity, the description of the invention is limited hereinafter to applications related to inspecting the internal surfaces of a hole in an object without requiring the object to be rotationally displaced. This however does not preclude embodiments of the invention from other areas of application that facilitates inspection of the interior of an object without requiring the object to be rotationally displaced. The fundamental inventive principles and concepts upon which embodiments of the invention are based shall remain common throughout the various embodiments.

An exemplary embodiment of the invention is described in greater detail hereinafter in accordance to illustrations provided in FIGS. 1 to 5 of the drawings, wherein like elements are identified with like reference numerals.

A method and apparatus for inspection is described hereinafter for addressing the foregoing problems.

Figure 1:
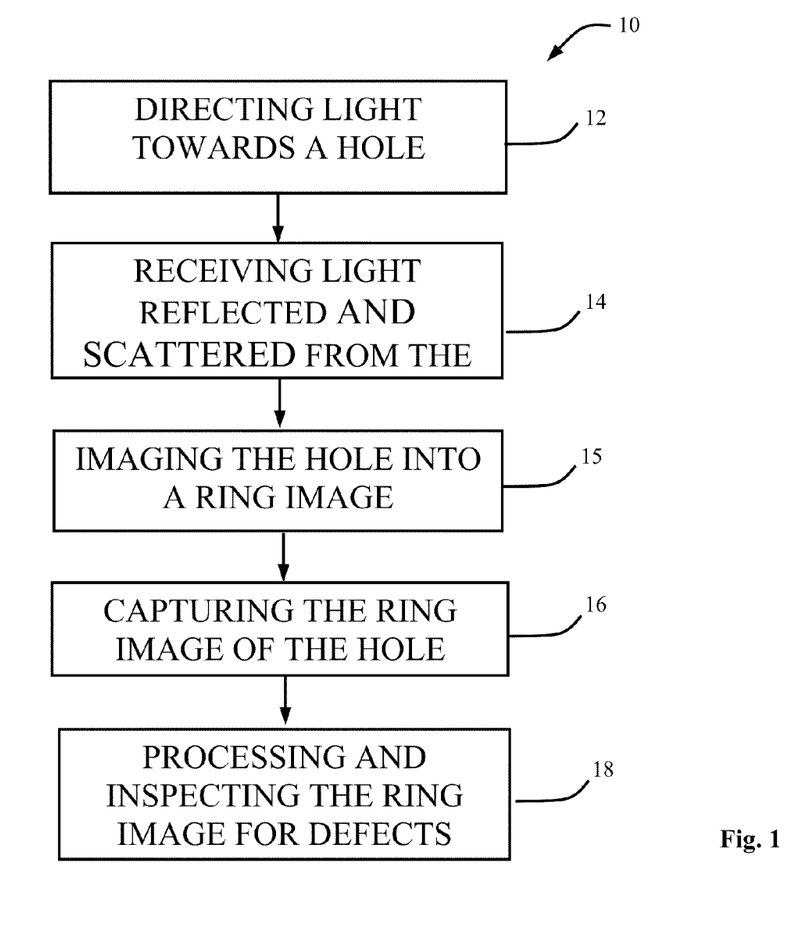
FIG. 1 is a flow diagram of a method for hole inspection according to a first embodiment of the invention.

FIG. 1 shows a flow diagram of a method 10 for inspecting a hole of an object, according to an exemplary embodiment of the invention. The method 10 involves a step 12 of directing an illuminating light towards the hole. The hole has two extremities and an internal surface that extends between the two extremities.

The method 10 also comprises a step 14 of directing light reflected and scattered from the internal surface of the hole to a lens assembly. The method 10 also comprises a step 15 of imaging of the internal surface of the hole into a flat ring image. The flat ring image shows full details of the internal surface of the hole. The method 10 also comprises a step 16 of capturing and converting the flat ring image from optical to digital form. The method 10 further comprises a step 18 of processing and inspecting the flat ring image to thereby inspect the internal surface of the hole.

In accordance with an exemplary embodiment of the invention, an apparatus 100 for inspection is described with reference to FIG. 2. The apparatus 100 comprises one or more illuminating source 102 for directing an illuminating light beam 103 towards a hole 104, which is cylindrical. The hole 104 is formed in an object 106, such as a through hole in a manufactured product. In this embodiment of the invention, illuminating sources 102 are used to direct light towards the hole 104.

The hole 104 has a first extremity 108, a second extremity 110 and an internal surface 112 that extends between the first and second extremities 108, 110. The first extremity 108 is closer to the apparatus 100 than the second extremity 110. The hole 104 is either a through hole or a blind hole. The illuminating sources 102 are operated accordingly to provide lighting to either the through hole or the blind hole.

The illuminating source 102 provides white, coloured or monochrome light for illuminating the hole 104. Examples of the illuminating source 102 are fluorescence light tubes and white, coloured, monochrome light emitting diodes (LEDs) or natural light from the sun. If the hole 104 is a through hole, the illumination is preferably directed as back lighting at the second extremity 110. On the other hand, if the hole 104 is a blind hole, the illumination is preferably directed at the first extremity 108.

The apparatus 100 also comprises a lens assembly 116. The illuminating light beam is reflected and scattered from the internal surface 112 of the hole 104 of FIG. 2 towards the lens assembly 116 The lens assembly 116 is preferably positioned immediately over the first extremity 108 of the hole 104.

Figure 2:
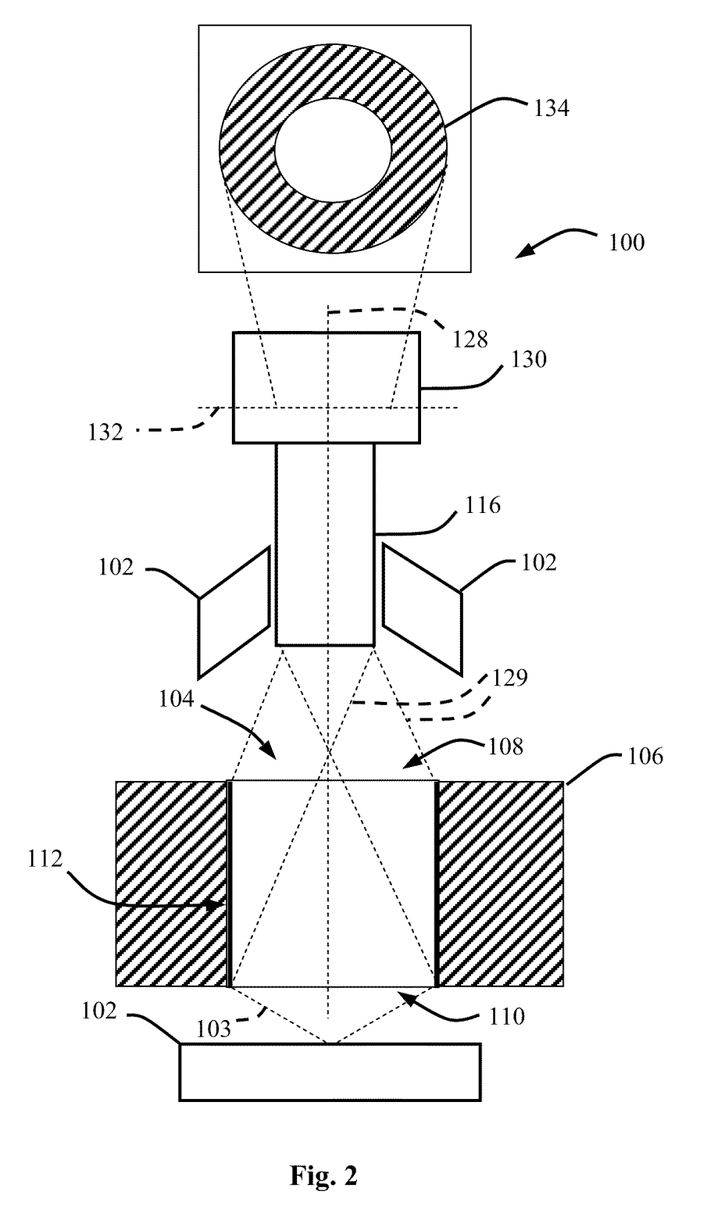
FIG. 2 is a cross-sectional view of an apparatus for hole inspection according to an embodiment of the invention.
Figure 3:
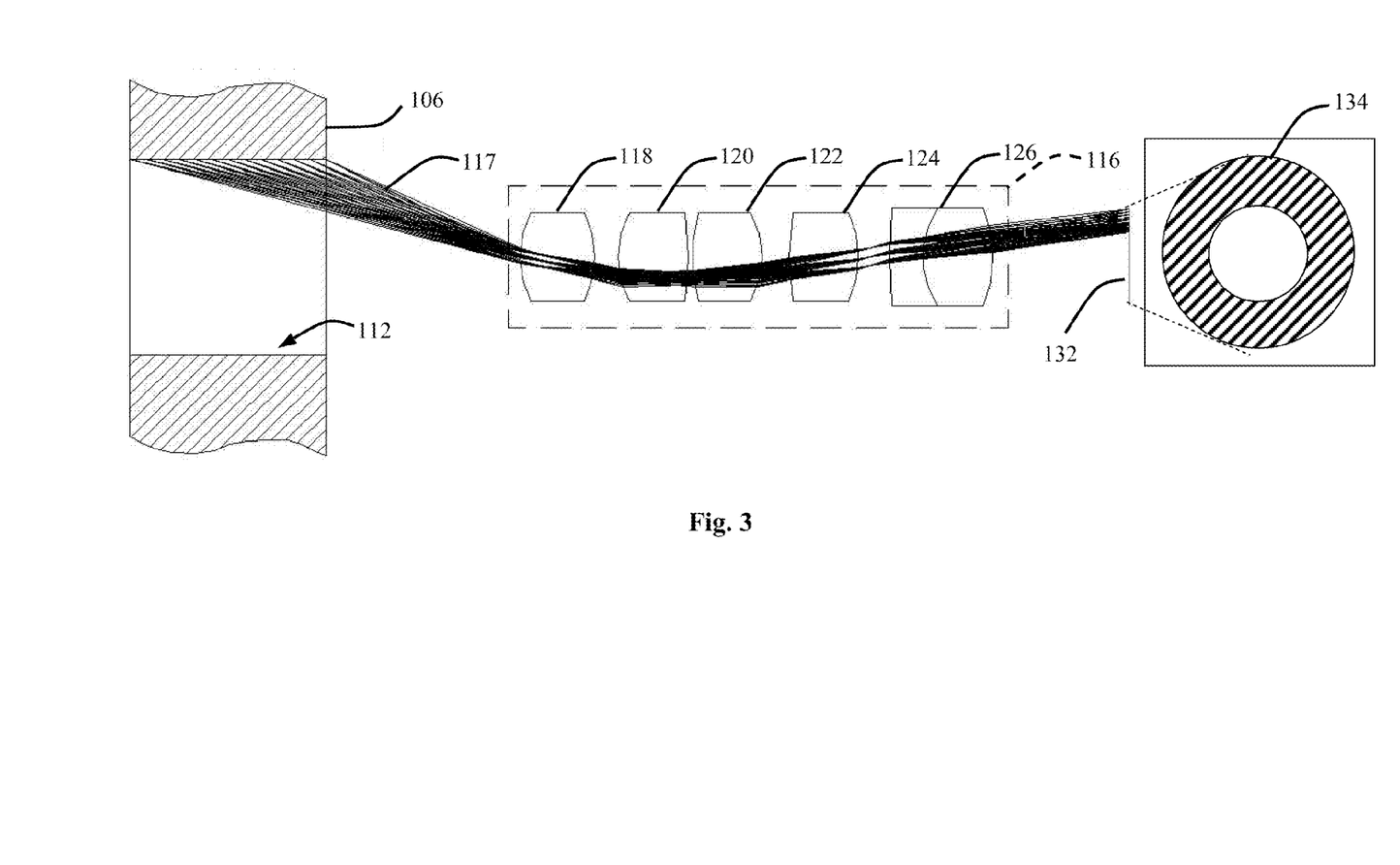
FIG. 3 is a cross-sectional view of a lens assembly of the apparatus of FIG. 2.

FIG. 3 is a detailed diagram of the lens assembly 116 of FIG. 2. FIG. 3 also shows paths of light rays 117 that pass through the lens assembly 116. More specifically, the lens assembly 116 of FIG. 3 comprises a plurality of lenses, namely a first lens 118, a second lens 120, a third lens 122, a fourth lens 124 and a fifth lens 126. Alternatively, the plurality of lenses is replaceable by prisms for achieving similar optical effects.

Each of the first to fifth lenses 118, 120, 122, 124, 126 preferably is positioned along a central axis 128 of the lens assembly 116. The central axis 128 preferably coincides with the longitudinal axis of the hole 104 of FIG. 2.

An exemplary example of the design of the lens assembly is described hereinafter. The specific dimensions of each of the first to fifth lenses 118, 120, 122, 124, 126 as well as the configuration of the lens assembly 116 are provided in Table 1 below.

TABLE 1

| Surface | Radius (mm) | Thickness (mm) | Diameter (mm) | Lens Type | Note |
|---|---|---|---|---|---|
| 1 | 6.0 | 5.1 | 5.4 | N-LAF21 | First lens |
| 2 | −6.0 | 0.4 | 5.4 | — | Space |
| 3 | 5.2 | 4.0 | 5.4 | N-LAF21 | Second lens |
| 4 | −20.0 | 0.2 | 5.4 | — | Space |
| 5 | 5.7 | 5.2 | 5.4 | F-SILICA | Third lens |
| 6 | −4.1 | 0.9 | 5.4 | — | Space |
| 7 | −88.8 | 5.0 | 5.4 | N-psk3 | Fourth lens |
| 8 | −6.1 | 0.2 | 5.4 | — | Space |
| 9 | inf | 4.0 | 0.6 | — | Aperture |
| 10 | 14.5 | 1.5 | 6.0 | N-SF11 | Fifth lens |
| 11 | 3.8 | 4.0 | 6.0 | N-LAK34 | Fifth lens |
| 12 | −10.5 | 8.8 | 6.0 | — | Space |

The lens assembly 116 is configurable for inspecting holes with a large dimensional range, such as holes with diameters ranging from 8 mm to 16 mm with depths ranging from 8 mm to 16 mm. In this exemplary of embodiment of the invention, the effective focal length of the lens assembly 116 is approximately 5.7 mm. The lens assembly 116 is capable of providing high quality image of the internal surface 112 of the hole 104.

The lens assembly 116 has a cylindrical field of view as well as a cylindrical depth of view that extends at least between the two extremities 108, 110 of the hole 104. The lens assembly 116 images the internal surface 112 of the cylindrical hole 104 into a flat ring image 134.

With reference to FIGS. 2 and 3, the apparatus 100 further comprises an image-capturing device 130, such as a camera, for capturing the flat ring image 134. The image-capturing device 130 is positioned along the central axis 128 of the lens assembly 116. An image sensor (not shown) of the image-capturing device 130 is positioned on an image plane 132 of the lens assembly 116. The ring image 134 of the internal surface 112 of the hole 104 between the two extremities 108, 110 is formed on the image plane 132. In particular, the internal surface 112 of the hole 104 between the two extremities 108, 110 is substantially in-focus along the flat ring image 134 on the image plane 132.

Figure 4:
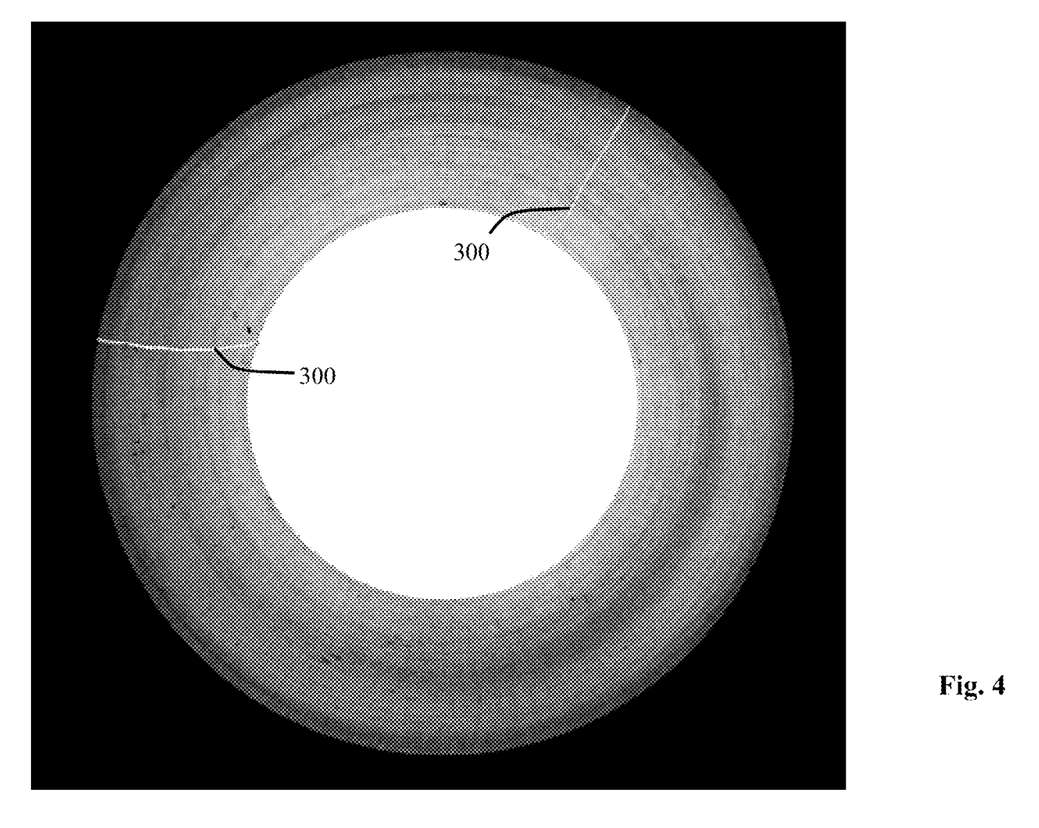
FIG. 4 is an image of a through-hole captured by the apparatus of FIG. 2 that uses back lighting.

The apparatus 100 is preferably connected to a computer (not shown) for image processing and for displaying the ring image 134 of the internal surface 112. For example, FIG. 4 shows a resultant image that is displayed on a displaying means (not shown) of the computer, such as a monitor, which shows a through-hole captured by the apparatus 100. More specifically, the resultant image depicts a focused ring image of the internal surface 112 of the hole 104 having defects 300 or scratches thereon.

Figure 5:
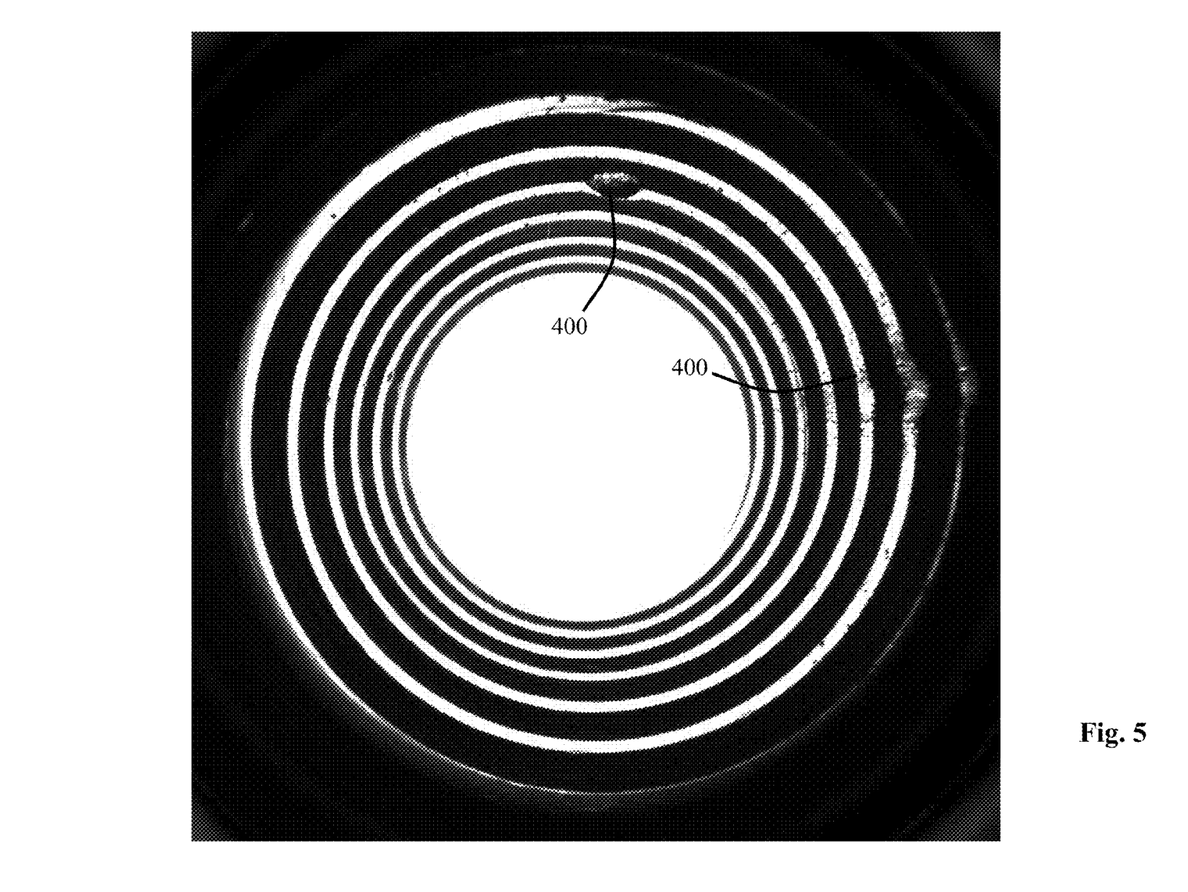
FIG. 5 is an image of a through-hole with screw nut tracks captured by the apparatus of FIG. 2 that uses back lighting.

In a further example, FIG. 5 shows another resultant image of a through-hole with screw nut threads as displayed on the displaying means. More specifically, some of the screw nut threads are shown clearly to have defective portions 400. The apparatus 100 is advantageously capable of identifying such defective portions 400 accurately and within a short period of time.

Inspection of the internal surface 112 of the hole 104 is preferably conducted by an image processing unit (not shown) using a software application. The image processing unit detects features such as screw nut threads on the surface of the hole and identifies and detects defects of the features. An indication is preferably shown on the displaying means for indicating the presence of the defects detected on the internal surface of the hole 104.

Additionally, the apparatus 100 is capable of determining the pitch $p_i$ of internal threads formed on the internal surface 112 of the hole 104 through image processing of the flat ring image 134 of FIG. 5. In particular, the pitch $p_i$ of internal threads and the radius $R_i$ of each spiral that corresponds to the internal threads at any radial direction are related as follows:

$$p_i = \left| \frac{R_0 - R_{i+1}}{k + b(R_0 - R_{i+1})} - \frac{R_0 - R_i}{k + b(R_0 - R_i)} \right|$$

where $R_0$, b and k are constants, i is the number of spiral threads formed on the internal surface 112 of the hole 104. $R_i$ and $R_{i+1}$ are radii of the spiral threads on the flat ring image 134 along the radial direction.

The apparatus 100 is further capable of inspecting defects on bond pads, bonding wires or interface therebetween of a semiconductor die. The semiconductor die is brought into the field of view of the apparatus 100 for inspecting the foregoing defects, similar to the method 10 for hole inspection.

In the foregoing manner, an apparatus and a method for hole inspection are described according to an exemplary embodiment of the invention for addressing the foregoing disadvantages of conventional method of performing inspection. Although only a few embodiments of the invention is disclosed, it will be apparent to one skilled in the art in view of this disclosure that numerous changes and/or modification can be made to cater to a wider range of hole sizes and heights without departing from the scope and spirit of the invention.

The invention claimed is:

1. An inspection method comprising:
providing an object having a cylindrical hole formed therein, the cylindrical hole having two extremities comprising a first extremity at which an opening of the hole resides and a second extremity, the hole further having a longitudinal axis and an internal surface extending from the first extremity to the second extremity, wherein the first extremity of the hole is above the second extremity of the hole along a central axis of a lens assembly, and wherein the central axis of the lens assembly coincides with the longitudinal axis of the hole;
disposing the hole in the presence of an illuminating light external to the hole, such that the illuminating light enters the hole through the opening at the first extremity of the hole and propagates within the hole in a direction toward the second extremity of the hole;
receiving by the lens assembly which is positioned outside of the hole and above the first extremity of the hole along the longitudinal axis of the hole portions of the illuminating light that entered the hole by way of the opening at the first extremity of the hole and which has propagated back out of the opening at the first extremity of the hole as a result of reflection and scattering from the internal surface of the hole, the lens assembly comprising a plurality of lens elements and having each of (i) a cylindrical field of view radially extending at least to the internal surface of the hole, as well as (ii) a cylindrical depth of field within which the internal surface of the hole from the first extremity of the hole to the second extremity of the hole is disposed;
imaging the internal surface of the hole between the two extremities of the hole into a flat ring image by way of propagation of the light received by the lens assembly therethrough, the flat ring image including full details of the internal surface of the hole from the first extremity of the hole to the second extremity of the hole;
capturing the flat ring image of the internal surface of the hole on an image plane such that the imaged internal surface of the hole from the first extremity of the hole to the second extremity of the hole is in-focus along the flat ring image; and
performing image processing of the captured flat ring image of the internal surface of the hole to thereby inspect the internal surface of the hole.

2. The inspection method as in claim 1, further comprising providing another illuminating light towards the hole.

3. The inspection method as in claim 1, wherein directing the illuminating light comprises directing one of white, coloured and monochrome light.

4. The inspection method as in claim 1, wherein performing inspection of the flat ring image to thereby inspect the internal surface of the hole comprising displaying the flat ring image on a computer monitor.

5. The inspection method as in claim 4, further comprising providing an indication on the computer monitor, wherein the indication relates to defects detected on the internal surface of the hole.

6. The inspection method as in claim 1, wherein performing inspection of the flat ring image to thereby inspect the internal surface of the hole comprises determining the depth of the hole.

7. The inspection method as in claim 1, wherein performing inspection of the flat ring image to thereby inspect the internal surface of the hole comprises determining the pitch of internal threads formed on the internal surface of the hole.

8. The method as in claim 1, further comprising bringing a semiconductor die into the cylindrical field of view of the lens assembly for inspection.

9. The method as in claim 8, further comprising inspecting defects on bond pads, bonding wires, or interfaces of the semiconductor die.

10. The method as in claim 1, wherein each point within the flat ring image that represents a point on the internal surface of the hole has an identical rotational orientation around a center point of the flat ring image as each point on the internal surface of the hole around the longitudinal axis of the hole.

11. An inspection apparatus comprising:
an object having a cylindrical hole therein, the hole having two extremities comprising a first extremity at which an opening of the hole resides and a second extremity, a longitudinal axis, and an internal surface extending from the first extremity of the hole to the second extremity of the hole, wherein the first extremity of the hole is above the second extremity of the hole along the longitudinal axis of the hole;
an illuminator outputting an illuminating light external to the hole and directing the illuminating light towards and into the opening of the hole at the first extremity of the hole along a direction toward the second extremity of the hole;
a lens assembly which is positioned outside of the hole and above the first extremity of the hole and having a central axis that coincides with the longitudinal axis of the hole, the lens assembly configured for (a) receiving portions of the illuminating light that entered the opening of the hole at the first extremity of the hole and which has propagated back out of the first opening of the hole after it has been reflected and scattered from the internal surface of the hole, and (b) imaging the internal surface of the hole into a flat ring image, the flat ring image including full details of the internal surface of the hole from the first extremity of the hole to the second extremity of the hole, the lens assembly comprising a plurality of lens elements and having each of (i) a cylindrical field of view around the longitudinal axis of the hole that radially extends to at least the internal surface of the hole, and (ii) a cylindrical depth of field within which the internal surface of the hole from the first extremity of the hole to the second extremity is disposed;
an image capturing device for capturing the flat ring image of the internal surface of the hole from the first extremity of the hole to the second extremity of the hole on an image plane, the internal surface of the hole from the first extremity of the hole to the second extremity of the hole being in-focus along the flat ring image on the image plane; and
a processor for performing image processing of the captured flat ring image of the internal surface of the hole to thereby inspect the internal surface of the hole.

12. The inspection apparatus as in claim 11, wherein a second illuminator directs an illuminating light towards the second extremity of the hole.

13. The inspection apparatus as in claim 11, further comprising another illuminator for illuminating light towards the hole.

14. The inspection apparatus as in claim 11, wherein the illuminating light is one of white, coloured and monochrome generated by the illuminator.

15. The inspection apparatus as in claim 11, wherein the illuminating light is natural light from the sun.

16. The inspection apparatus as in claim 11, wherein the plurality of lens elements is disposed along the central axis of the lens assembly which coincides with the longitudinal axis of the hole.

17. The inspection apparatus of claim 11, wherein the image capturing device is coupled to a computer monitor for displaying the flat ring image.

18. The inspection apparatus as in claim 17, wherein the image capturing device is disposed adjacent to the lens assembly for capturing the flat ring image.

19. The inspection apparatus as in claim 17, further comprising an indicator displayable on the computer monitor, the indicator for indicating defects detected on the internal surface of the hole.

20. The inspection apparatus as in claim 11, wherein processing unit executing a software application inspects the flat ring image corresponding to the internal surface of the hole.

21. The inspection apparatus as in claim 20, wherein the processing unit executing the software application determines the depth of the hole.

22. The inspection apparatus as in claim 20, wherein the image processing unit executing the software application determines the pitch of internal threads formed on the internal surface of the hole.

23. The inspection apparatus as in claim 11, wherein the lens assembly is configured to image each point on the internal surface of the hole around the longitudinal axis of the hole to a corresponding point within the flat image such that each point within the flat ring image that represents a point on the internal surface of the hole has an identical rotational orientation around a center point of the flat ring image as each point on the internal surface of the hole around the longitudinal axis of the hole.

* * * * *